United States Patent [19]

Brodowski et al.

[11] Patent Number: 5,417,962
[45] Date of Patent: May 23, 1995

[54] USNIC ACID DEODORANT STICK

[75] Inventors: Michael H. Brodowski, Brookline; Michael G. White, South Boston, both of Mass.

[73] Assignee: The Gillette Company, Boston, Mass.

[21] Appl. No.: 70,319

[22] Filed: Jun. 2, 1993

Related U.S. Application Data

[63] Continuation-in-part of Ser. No. 824,987, Jan. 24, 1992, abandoned.

[51] Int. Cl.$^6$ .......................... A61K 7/32; A61K 35/78
[52] U.S. Cl. ................................. 424/65; 424/DIG. 5; 424/195.1
[58] Field of Search ............................ 424/65, 195.1

[56] References Cited

U.S. PATENT DOCUMENTS

| 3,507,807 | 4/1970 | Palikko | 252/389 |
|---|---|---|---|
| 4,814,165 | 3/1989 | Berg et al. | 424/DIG. 5 |
| 4,892,727 | 1/1990 | Grollier | 424/DIG. 5 |
| 4,921,694 | 5/1990 | Hoppe et al. | 424/DIG. 5 |
| 5,256,405 | 10/1993 | Chappell et al. | 424/65 |

FOREIGN PATENT DOCUMENTS

| 2351927 | 10/1973 | Germany | 424/65 |
|---|---|---|---|
| 2354517 | 10/1973 | Germany | 424/65 |
| 2351864 | 4/1975 | Germany | 424/65 |
| 2432484 | 1/1976 | Germany | 424/65 |

OTHER PUBLICATIONS

Bergerhausen, *Cosmetics and Toiletries, Deodorizing Action of a Complex of Usnic Acid*, vol. 1, pp. 25–26 Feb. 1976.

Heine et al., *Allergisches Kontaktekzen durch Usinsaure in Deodorantsprays*, 16 Dermatol Mon.schr. Band Heft 4.

Fontana et al., *American Chemical Society, L'Acido Usnico come preservante naturale, deodorante e dermopurificante nei sistemi cosmetici (Usnic Acid as Natural Preservative deodorant, and Antimicrobial Agent in Cosmetic Systems)*, pp. 315–336, 1974.

Bergerhausen, Cosmetics and Toiletries 91:25 (1976).

Deo-Usnate, Cosmetochem Brochure (date unknown, 1991 or earlier) No specific date thereon.

*Primary Examiner*—Dale R. Ore
*Attorney, Agent, or Firm*—Stephan P. Williams

[57] ABSTRACT

A solid deodorant stick product comprises from about sixty-five percent to about eighty-five percent of an aliphatic polyhydric alcohol, from about three percent to about twelve percent of a gel forming agent; and from about 0.05 to about 0.2 percent usnic acid; the composition having a chromatogram made by high pressure liquid chromatography with an usnic acid peak and a degradation constituent peak, the area of the usnic acid peak being at least ten times the area of the degradation constituent peak (FIG. 2).

10 Claims, 1 Drawing Sheet

USNIC ACID DEODORANT STICK

This application is a continuation-in-part of Ser. No. 07/824,987 filed Jan. 24, 1992, now abandoned. This case has priority under 35 USC 371 based on PCT/US92/11297 filed Jan. 24, 1992.

This invention relates to cosmetic products, and more particularly to solid deodorant products and to processes for forming such deodorant products.

It is known that bacterial decomposition of apocrine sweat produces an unpleasant odor that develops in the axillae. A large number of products for reducing such odors are on the market. Many such deodorant products have been based on the use of germicides such as hexachlorophene and various quaternary ammonium compounds. The deodorizing action of usnic acid has also been recognized. Usnic acid is an organic compound that conforms to the formula: 2,6-diacetyl-7,9-dihydroxy-8,9b-dimethyl-1,3(2H,9bH)-dibenzofurandione and is extracted from alpine lichen (usnea barbara). Usnic acid has a high level of antimicrobial activity against odor producing bacteria. When formulated into compositions of the deodorant stick type, however, such sticks tend to undergo an extreme color change (from a translucent light color to a dark brown color). Such color change is commercially undesirable due to adverse consumer reaction. A deodorant stick preferably is of light translucent color such as amber or pale blue/green and retains that color characteristic throughout its useful life including shelf storage and consumer use.

In accordance with one aspect of the invention, there is provided a solid deodorant stick product that comprises from about sixty-five percent to about eighty-five percent of an aliphatic polyhydric alcohol, from about three percent to about twelve percent of a gel forming agent; and from about 0.05 to about 0.2 percent usnic acid; the composition is characterized in that a chromatogram thereof made by high pressure liquid chromatography equipped with an ultraviolet detector measuring absorbance at a wavelength of 282 nanometers has an usnic acid peak and a degradation constituent peak, the area of the usnic acid peak being at least ten times the area of the degradation constituent peak. In particular embodiments, the column is a reverse phase C18 column packed with irregularly-shaped silica having a surface area of at least 100 square meters per gram and bonded with C18 carbon with a flow rate of two milliliters per minute and a pressure of approximately 8.3 megapascals (1,200 psig), the degradation constituent is produced at a retention time of approximately 1.9 minutes while the usnic acid peak is produced at a retention time of approximately 3.3 minutes.

An essential ingredient of the compositions hereof is usnic acid—a natural antimicrobial derived from lichens. Usnic acid (2,6-diacetyl-7,9-dihydroxy-8,9b-dimethyl-1,3(2H,9bH)-dibenzofurandione) has the following structure:

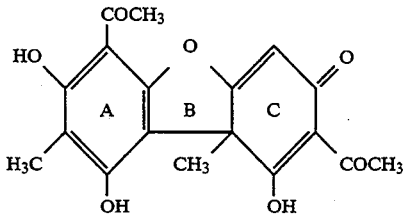

Solutions of usnic acid in solvents such as propylene glycol tend to undergo extreme color change from pale yellow to reddish-brown. The usnic acid solution apparently has a degradation constituent which may increase in magnitude but if this degradation constituent is kept small, the resulting cosmetic product has commercially-acceptable color stability—that is, it does not darken unacceptably over its useful life, both in terms of shelf and in terms of consumer use life. Compositions in accordance with the invention thus are made by employing an usnic acid solution in which the degradation constituent in terms of chromatographic peak area is less than one tenth the usnic acid peak area. By minimizing the amount of the degradation constituent of the composition, enhanced color stability is achieved.

Another essential component of the present deodorant gel stick compositions is a polyhydric aliphatic alcohol containing 2 to 6 carbon atoms, preferably 2 or 3, and from 2 to 6 hydroxyl groups, preferably 2 to 3. The polyhydric aliphatic alcohol component of the stick comprises from about 65 to 85 percent, preferably from about 70 to 80 percent by weight of the composition. Suitable polyhydric alcohols for use in the gel compositions hereof include ethylene glycol, propylene glycol, trimethylene glycol, glycerine and mixtures thereof. The most preferred polyol is propylene glycol. The composition may also include five to twenty-five percent water (preferably ten to twenty percent) primarily for aesthetic purposes such as glide or feel.

A third essential component of the deodorant stick compositions hereof is a gel-forming agent which is added to the polyhydric aliphatic alcohol. The gel-forming agents used herein are preferably the sodium, potassium and aluminum salts (i.e., soaps) of fatty acids containing from about 14 to 22 carbon atoms. The gel-forming agents generally comprise from about three percent to about twelve percent by weight, preferably from about three percent to about eight percent by weight of the composition. If lower gel-forming agent concentrations are employed, the gels formed tend to be dimensionally unstable and tend to deform at summertime temperatures. If higher gel-forming agent concentrations are utilized, the gels formed tend to be too hard and do not exhibit desirable gliding application characteristics. The fatty acid portion of the soap gel forming agents preferably are essentially pure saturated or unsaturated higher fatty acids having a $C_{14}$ to $C_{22}$ backbone. Suitable mixtures of such acids can be employed. Examples of fatty acids useful herein include myristic, palmitic, stearic, oleic, linoleic, behenic, and margaric acids and mixtures of such acids. Naturally occurring sources of such fatty acids include coconut oil, beef tallow, lanolin, fish oil, beeswax, palm oil, peanut oil, olive oil, soybean oil, corn oil, rape seed oil, and rosin acids. Preferred fatty acid gel-forming agents includes sodium stearate, sodium palmitate, potassium stearate, potassium palmitate, and sodium myristate, the most preferred gel-forming agent being sodium stearate. Unless otherwise indicated, all percentages herein are by weight.

The composition can include a variety of optional ingredients suitable for improving composition efficacy, stability, and/or aesthetics. Such optional components include perfumes, dyes, pigments, coloring agents and the like.

In accordance with another aspect of the invention, there is provided a process of producing a solid deodorant stick product that comprises the steps of providing an aliphatic polyhydric alcohol, heating the aliphatic polyhydric alcohol to a temperature of about 75° C., adding a gel-forming agent, stirring the resulting mixture until the gel-forming agent dissolves; cooling the mixture; adding an usnic acid solution at a temperature of about 70° C., and pouring said resulting mixture into a suitable container, the resulting solid product having excellent deodorant effectiveness and color stability and having from about sixty-five to about eighty-five percent of the aliphatic polyhydric alcohol, from about three percent to about twelve percent of the gel-forming agent; and from about 0.05 to about 0.2 percent of usnic acid; and both the usnic acid solution and the resulting stick product having chromatograms made by high pressure liquid chromatography equipped with an ultraviolet detector measuring absorbance at a wavelength of 282 nanometers with an usnic acid peak and a degradation constituent peak, the area of each usnic acid peak being at least ten times the area of the corresponding degradation constituent peak.

In accordance with another aspect of the invention, there is provided a method of making multiple commercial batches of a solid deodorant stick product comprising about 0.05 to about 0.5% usnic acid in a solid deodorant stick base, the solid deodorant stick product having consistently good color quality and color stability from batch to batch. The method comprises the steps of mixing a solution of usnic acid with the liquefied components of the deodorant stick base at a temperature of 70° C. or less, pouring the resulting mixture into suitable containers and cooling to form solid deodorant stick products, the usnic acid solution having a Gardner color of 13 or less and producing an HPLC chromatogram which contains an usnic acid peak and a degradation constituent peak, the area of the usnic acid peak being at least ten times the area of the degradation constituent peak. By commercial batch is meant a quantity greater than fifty gallons, preferably on the order of 500–2000 gallons. By consistently good color quality and color stability is meant a product which has a translucent (to almost clear) amber color (in the absence of other dyes) when manufactured and which primarily retains that color, and does not turn muddy brown, when stored at room temperature for one year, preferably one and a half years.

Preferably, the usnic acid solution has a Gardner color of 10 or less and produces an HPLC chromatogram in which the area of the usnic acid peak is at least twenty times the area of the degradation constituent peak; the solid deodorant stick base comprises about 65 to 85% of an aliphatic polyhydric alcohol, about 3 to 12% of a gel-forming agent, and 5 to 25% water.

In preferred embodiments, the chromatogram is made with a reverse phase C18 column 25 centimeters long by 4.6 millimeter inner diameter packed with irregularly shaped silica (ten micron particle size) with a surface area of about 450 square meters per gram bonded with C18 carbon and a pore diameter of 60 angstroms (Alltech Catalog #60148 or equivalent). The mobile phase is 85 percent aqueous acetonitrile with 0.1 percent phosphoric acid. Elution is at a flow rate of two milliliters per minute and a pressure of approximately 8.3 megapascals (1200 psig). A diluted sample volume of twenty microliters is injected into the column and the chromatogram is obtained, the degradation peak being produced at least about one minute prior to the usnic acid peak. Naturally, of course, other HPLC techniques which use different column materials, eluents and flow rates will likely place the degradation constituent peak and the usnic acid peak in slightly different locations in the chromatogram, but the area ratio can nonetheless be measured so long as the peaks are adequately resolved. Thus, the reference herein to a chromatogram similar to FIG. 1 does not mean identical to FIG. 1, but simply means a chromatogram which resolves the degradation constituent peak and the usnic acid peak in a manner like that shown in FIG. 1.

In a particular embodiment, the polyhydric aliphatic alcohol is propylene glycol and comprises from about seventy to about eighty percent of the product; the gel-forming agent is sodium stearate and comprises from about three to about eight percent by weight of the product; and the product contains ten to twenty percent water.

Other features and advantages of the invention will be seen as the following description of particular embodiments progresses, in conjunction with the drawings, in which.

DESCRIPTION OF PARTICULAR EMBODIMENTS

Figure 1:
FIG. 1 is a chromatogram of an usnic acid solution with a degradation peak at 1.88 minutes and an usnic acid peak at 3.21 minutes.

FIG. 1 is a chromatogram of an usnic acid solution (DEO-USNATE—CTFA—propylene glycol (and) lichen extract) that has a Gardner color of about 7. That solution is commercially available from Cosmetochem AG, Cham, Switzerland and has two parts usnic acid, one part of a solubilizing amine component and thirty-seven parts propylene glycol.

The solution was subjected to high pressure liquid chromatography using an ultraviolet detector measuring absorbance at a wavelength of 282 nanometers. A reverse phase C18 column 25 centimeters long by 4.6 millimeter inner diameter was packed with irregularly shaped silica (ten micron particle size) with a surface area of about 450 square meters per gram bonded with C18 carbon and a pore diameter of 60 angstroms (Alltech Catalog #60148 or equivalent). The mobile phase was 85 percent aqueous acetonitrile with 0.1 percent phosphoric acid. Elution was at a flow rate of two milliliters per minute and a pressure of approximately 8.3 megapascals (1200 psig). A diluted sample volume of twenty microliters (0.065% sample, approximately 0.0025–0.0030 wt. % usnic acid) was injected into the column and the chromatogram of FIG. 1 was obtained. That chromatogram has a void peak 10 at 1.22 minutes, a degradation peak 12 at 1.88 minutes and an usnic acid peak 14 at 3.21 minutes. The ratio of the areas under peaks 12, 14 was 0.028.

A stick composition had the following components:

| Constituents | Percent by Weight |
|---|---|
| Propylene glycol | 78.40 |
| Deionized water | 15.00 |
| Sodium strearate | 6.50 |
| Usnic Acid (from DEO-USNATE) | 0.10 |
| | 100.0 |

The starting color of the propylene glycol/lichen extract solution was 13 on the Gardner color scale; and the formulation did not include fragrance or dye to avoid chromatographic interferences that may be created by those constituents.

The product was made by mixing propylene glycol and water and heating to 75° C. The sodium stearate was added at about 75° C., and the mixture was held with gentle stirring until the sodium stearate dissolved. The mixture then was cooled slowly with the lichen extract solution being added at about 70° C.; and the mixture then poured into a suitable container. The resulting stick product was of light amber color and had excellent deodorant effectiveness and color stability.

0.6 gram of the resulting stick product was dissolved in methanol with heating on a steam bath. The resulting liquid was diluted to 25 milliliters total volume with acetonitrile and the solution was filtered through a 0.45 micron Gelman Acrodisc CR filter.

Figure 2:
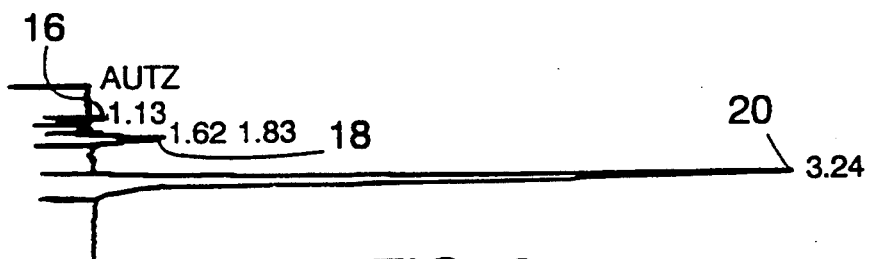
FIG. 2 is a chromatogram of a cosmetic stick composition in accordance with the invention which shows the presence of the degradation constituent.

The resulting filtered solution (2.4% product, approximately 0.0025–0.0030 wt. % usnic acid) was then subjected to high pressure liquid chromatography using an ultraviolet detector measuring absorbance at a wavelength of 282 nanometers as previously described and the chromatogram of FIG. 2 was obtained. That chromatogram has a void peak 16 at 1.13 minutes, a degradation peak 18 at 1.83 minutes and an usnic acid peak 20 at 3.24 minutes. The ratio of the areas of peaks 18, 20 was 0.078.

Another deodorant stick composition had the following constituents:

| Constituents | Percent by Weight |
|---|---|
| Propylene glycol | 77.30 |
| Deionized water | 14.99945 |
| Sodium stearate | 6.50 |
| Usnic Acid (from DEO-USNATE) | 0.10 |
| Perfume | 1.10 |
| Blue #1 dye | 0.00055 |
| | 100.00 |

The starting color of the propylene glycol/lichen extract solution was about 12 on the Gardner color scale.

The product was made by mixing propylene glycol, dye and water and heating to 75° C. The sodium stearate was added at about 75° C., and the mixture was held with gentle stirring until the sodium stearate dissolved. The mixture then was cooled slowly with the lichen extract solution being added at about 70° C.; fragrance then being added as the mixture continues to cool; and the mixture then poured into a suitable container. The resulting stick product was of light blue/green color and had excellent deodorant effectiveness and color stability.

0.6 gram of the resulting stick product was dissolved in methanol with heating on a steam bath. The resulting liquid was diluted to 25 milliliters total volume with acetonitrile and the solution was filtered through a 0.45 micron Gelman Acrodisc CR filter.

Figure 3:
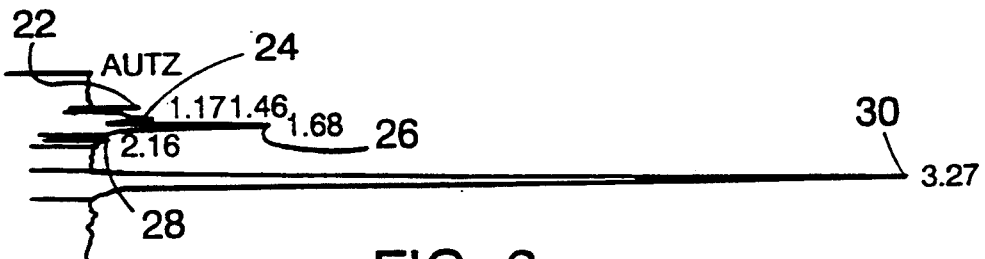
FIG. 3 is a chromatogram of a second cosmetic stick composition in accordance with the invention.

The resulting filtered solution was then subjected to high pressure liquid chromatography using an ultraviolet detector measuring absorbance as previously described and the chromatogram of FIG. 3 was obtained. That chromatogram has a void peak 22 at 1.17 minutes, a series of peaks 24, 26, 28 at 1.46, 1.68 and 2.16 minutes, respectively and an usnic acid peak 30 at 3.27 minutes. The peaks 24, 26, 28 obscure the degradation peak and are believed due to the fragrance and/or dye constituents. A chromatogram of the deodorant stick product of this example without the fragrance and dye constituents shows the degradation constituent peak and has a peak area ratio of less than 0.1.

Another deodorant stick composition had the following constituents:

| Constituents | Percent by Weight |
|---|---|
| Propylene glycol | 77.55 |
| Deionized water | 14.99945 |
| Sodium stearate | 6.50 |
| Usnic Acid (from DEO-USNATE) | 0.10 |
| Perfume | 0.85 |
| Blue #1 dye | 0.00055 |
| | 100.00 |

The starting color of the DEO-USNATE propylene glycol/lichen extract solution was about 4 on the Gardner color scale. The DEO-USNATE solution was manufactured by Cosmetochem AG and was stored in opaque polyethylene containers and maintained at a temperature in the range between −8° F. and 45° F. until used. A one thousand gallon batch of the above composition was made by mixing propylene glycol, dye and water and heating to 75° C. The sodium stearate was added at about 75° C., and the mixture was held with gentle stirring until the sodium stearate dissolved. The mixture then was cooled slowly with the lichen extract solution and fragrance being added at about 70° C.; and the mixture then poured into approximately forty thousand (of ninety grams capacity each) containers. The resulting stick product was of light blue/green color and had deodorant effectiveness and color stability.

Figure 4:
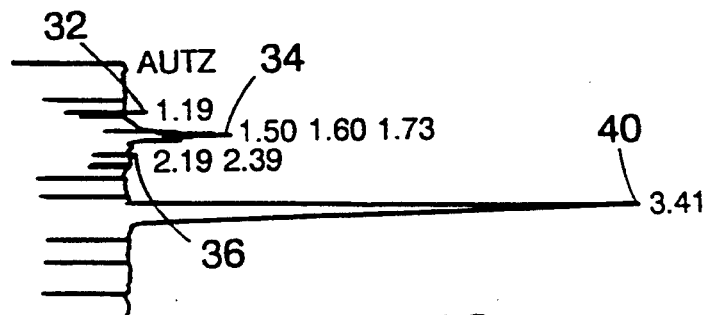
FIG. 4 is a chromatogram of another cosmetic stick composition in accordance with the invention.

0.6 gram of the resulting stick product was dissolved in methanol with heating on a steam bath. The resulting liquid was diluted to 25 milliliters total volume with acetonitrile and the solution was filtered through a 0.45 micron Gelman Acrodisc CR filter. The resulting filtered solution was then subjected to high pressure liquid chromatography as previously described, and the chromatogram of FIG. 4 was obtained. That chromatogram has a void peak 32 at 1.19 minutes, a series of peaks 34, 36 at 1.50, 1.60, 1.73, 2.19 and 2.39 minutes, respectively and an usnic acid peak 40 at 3.41 minutes. The peaks 34, 36 obscure the degradation peak and are believed due to the fragrance and/or dye constituents. A chromatogram of the deodorant stick product of this example without the fragrance and dye constituents would show the degradation constituent peak and have a peak area ratio of less than 0.1.

While particular embodiments of the invention has been shown and described, various modifications will be apparent to those skilled in the art, and therefore, it is not intended that the invention be limited to the disclosed embodiments, or to details thereof, and departures may be made therefrom within the spirit and scope of the invention.

We claim:

1. In a method for making multiple commercial batches of a solid usnic acid deodorant stick product comprising about 0.05 to about 0.5% usnic acid in a solid deodorant stick base, which method comprises mixing a solution of usnic acid with the liquefied components of said deodorant stick base, pouring the resulting mixture into suitable containers and cooling to form solid deodorant stick products, wherein the improvement comprises conducting said mixing at a temperature of 70° C. or less and utilizing an usnic acid solution which has a Gardner color of 13 or less and produces an HPLC chromatogram which contains an usnic acid peak and a degradation constituent peak, the area of said usnic acid peak being at least ten times the area of said degradation constituent peak, whereby said solid deodorant stick product has consistently good color quality and color stability from batch to batch.

2. The method of claim 1, wherein the usnic acid solution has a Gardner color of 10 or less and produces an HPLC chromatogram in which the area of the usnic acid peak is at least twenty times the area of the degradation constituent peak.

3. The method of claim 1, wherein the solid deodorant stick base comprises about 65 to 85% of an aliphatic polyhydric alcohol, about 3 to 12% of a gel-forming agent, and 5 to 25% water.

4. The method of claim 3, wherein the aliphatic polyhydric alcohol is selected from ethylene glycol, propylene glycol, trimethylene glycol, glycerins, and mixtures thereof and the gel-forming agent is selected from sodium, potassium and aluminum salts of fatty acids containing from about 14 to 22 carbon atoms.

5. The method of claim 4, where the solid deodorant stick base comprises about 10 to 20% water.

6. The method of claim 5, wherein the aliphatic polyhydric alcohol is propylene glycol and the gel-forming agent is sodium stearate.

7. The method of claim 1, 2, 3, 4, 5 or 6, wherein the HPLC chromatogram is similar to that shown in FIG. 1.

8. The method of claim 1, 2, 3, 4, 5 or 6, wherein the HPLC chromatogram is obtained by passing a twenty microliter sample of usnic acid solution in acetonitrile through a reverse phase C18 column, 25 centimeter long by 4.6 millimeters inner diameter packed with irregularly shaped silica, bonded with C18 carbon, of about ten micron particle size with a surface area of about 450 square meters per gram and a pore diameter of about six nanometers, using as eluent 85% aqueous acetonitrile with 0.1% phosphoric acid at a flow rate of two milliliters per minute and a pressure of about 8.3 megapascals, and using an ultraviolet detector measuring absorbance at a wavelength of 282 nanometer.

9. A solid deodorant stick product made in accordance wit claim 1, 2, 3, 4, 5 or 6.

10. A solid deodorant stick product made in accordance with claim 7.

* * * * *